US010239685B2

(12) United States Patent
Dann et al.

(10) Patent No.: US 10,239,685 B2
(45) Date of Patent: Mar. 26, 2019

(54) SPRAY DELIVERY DEVICE

(71) Applicant: Mission Pharmacal Company, San Antonio, TX (US)

(72) Inventors: Thomas Dann, Oldsmar, FL (US); Renee Nelson, Brandon, FL (US); Brian Wagner, Henderson, NV (US); Mary Walter, Vancouver, WA (US)

(73) Assignee: Mission Pharmacal Company, San Antonio, TX (US)

(*) Notice: Subject to any disclaimer, the term of this patent is extended or adjusted under 35 U.S.C. 154(b) by 0 days.

(21) Appl. No.: 14/619,127

(22) Filed: Feb. 11, 2015

(65) Prior Publication Data

US 2015/0232260 A1 Aug. 20, 2015

Related U.S. Application Data

(60) Provisional application No. 61/939,830, filed on Feb. 14, 2014.

(51) Int. Cl.
*B65D 83/38* (2006.01)
*B65D 83/14* (2006.01)
(Continued)

(52) U.S. Cl.
CPC .......... *B65D 83/752* (2013.01); *A61K 9/0014* (2013.01); *A61K 9/124* (2013.01);
(Continued)

(58) Field of Classification Search
CPC ......... B65D 83/38; B65D 83/48; B65D 83/20
(Continued)

(56) References Cited

U.S. PATENT DOCUMENTS 3,770,648 A 11/1973 Mackles
4,099,703 A * 7/1978 Lush ........................ F16K 1/52 251/122
(Continued)

FOREIGN PATENT DOCUMENTS

CA 1088428 10/2008
EP 0 531 044 A1 3/1993
(Continued)

OTHER PUBLICATIONS

Honeywell, Physical-properties-comparison-table, https://www.honeywell-solstice-propellants.com/ResourceCenter/Documents/Honeywell-HFO1234ze-HFC-134a-physical-properties-comparison-table.pdf.*
(Continued)

*Primary Examiner* — Chee-Chong Lee
(74) *Attorney, Agent, or Firm* — Dority & Manning, P.A.

(57) ABSTRACT

A spray delivery system including a sprayable active agent composition housed within a container is provided that can be used in the treatment of various skin conditions. The composition includes a hydrofluoro-based propellant, a carrier fluid, and active agent particles, and has a viscosity ranging from about 500 centipoise to about 10,000 centipoise. The container includes a dip tube; a valve assembly that includes a valve body, a stem comprising a stem orifice, and a vapor tap; and an actuator. The dip tube is coupled to the actuator by the valve assembly, and the actuator is depressed to dispense the emulsion. By selectively controlling the components and viscosity of the composition and the dimensions of the container components, the active agent particles resist settling so a substantially homogeneous distribution of the particles is maintained. Thus, the composition can be evenly dispensed from the container as a fine mist without clogging.

22 Claims, 4 Drawing Sheets

(51) Int. Cl.

| | |
|---|---|
| ***A61K 9/12*** | (2006.01) |
| ***A61K 9/00*** | (2006.01) |
| ***A61K 47/06*** | (2006.01) |
| ***A61K 33/30*** | (2006.01) |
| ***A61K 47/24*** | (2006.01) |
| ***A61K 47/26*** | (2006.01) |
| ***B65D 83/48*** | (2006.01) |
| ***B65D 83/20*** | (2006.01) |
| *B65D 83/32* | (2006.01) |
| *B05B 7/04* | (2006.01) |

(52) U.S. Cl.
CPC .............. *A61K 33/30* (2013.01); *A61K 47/06* (2013.01); *A61K 47/24* (2013.01); *A61K 47/26* (2013.01); *B65D 83/206* (2013.01); *B65D 83/48* (2013.01); *B05B 7/0483* (2013.01); *B65D 83/32* (2013.01)

(58) Field of Classification Search
USPC ........................................ 239/337; 222/402.1
See application file for complete search history.

(56) References Cited

U.S. PATENT DOCUMENTS

| | | | | | |
|---|---|---|---|---|---|
| 4,155,864 | A * | 5/1979 | Martin | C08L 83/04 252/573 |
| 4,174,386 | A * | 11/1979 | Spitzer | A61K 8/046 424/45 |
| 4,230,243 | A * | 10/1980 | Spitzer | B65D 83/14 222/402.18 |
| 4,439,342 | A * | 3/1984 | Albanese | C09D 5/021 106/10 |
| 4,439,343 | A * | 3/1984 | Albanese | C09D 5/02 106/10 |
| 4,808,323 | A * | 2/1989 | Fisher | C10M 111/02 508/583 |
| 4,981,677 | A | 1/1991 | Thau | |
| 5,143,288 | A | 9/1992 | Kohler et al. | |
| 5,286,475 | A | 2/1994 | Louvet et al. | |
| 5,871,756 | A | 2/1999 | Jeffcoat et al. | |
| 6,047,946 | A | 4/2000 | Kolanus | |
| 6,165,450 | A | 12/2000 | Chaudhuri et al. | |
| 6,345,775 | B1 | 2/2002 | Purvis, II et al. | |
| 6,394,321 | B1 | 5/2002 | Bayer | |
| 6,627,178 | B1 | 9/2003 | Cawthon | |
| 6,949,249 | B2 | 9/2005 | Healy et al. | |
| 7,241,805 | B2 | 7/2007 | Oberegger et al. | |
| 8,087,548 | B2 | 1/2012 | Kimball | |
| 8,440,171 | B2 | 5/2013 | Valpey, III et al. | |
| 8,465,728 | B2 | 6/2013 | Tasz et al. | |
| 2004/0184992 | A1 | 9/2004 | Abram | |
| 2005/0244342 | A1 | 11/2005 | Friedman et al. | |
| 2005/0255048 | A1 | 11/2005 | Hirsh et al. | |
| 2006/0034937 | A1 | 2/2006 | Patel | |
| 2006/0165603 | A1 | 7/2006 | Meakin et al. | |
| 2008/0031907 | A1 | 2/2008 | Tamarkin et al. | |
| 2008/0152681 | A1 | 6/2008 | Brown et al. | |
| 2008/0194494 | A1 * | 8/2008 | Martinez | C07D 205/08 514/25 |
| 2009/0257957 | A1 | 10/2009 | Burnier et al. | |
| 2011/0014135 | A1 | 1/2011 | Buchta et al. | |
| 2011/0150792 | A1 | 6/2011 | Shao et al. | |
| 2011/0240683 | A1 | 10/2011 | Stegeman | |
| 2012/0058973 | A1 | 3/2012 | Narasimhan et al. | |
| 2012/0219634 | A1 | 8/2012 | Maslowski et al. | |
| 2013/0058985 | A1 | 3/2013 | Willems et al. | |
| 2013/0078191 | A1 | 3/2013 | Teramoto et al. | |
| 2013/0115173 | A1 | 5/2013 | Trumbore et al. | |
| 2013/0164226 | A1 | 6/2013 | Nakamoto | |
| 2013/0233310 | A1 | 9/2013 | Hilgers et al. | |
| 2013/0237613 | A1 | 9/2013 | Kim | |
| 2013/0251644 | A1 | 9/2013 | Majhi et al. | |
| 2013/0303615 | A1 | 11/2013 | Scholz et al. | |
| 2014/0243299 | A1 | 8/2014 | Gurge et al. | |
| 2015/0231071 | A1 | 8/2015 | Dann et al. | |
| 2015/0231072 | A1 | 8/2015 | Dann et al. | |

FOREIGN PATENT DOCUMENTS

| | | | |
|---|---|---|---|
| EP | 0 937 451 | A2 | 8/1999 |
| JP | 2006213409 | A | 8/2006 |
| JP | 2012197359 | A | 10/2012 |
| WO | WO 2004/037225 | A2 | 5/2004 |
| WO | WO 2007/039825 | A2 | 4/2007 |
| WO | WO 2008/002428 | A1 | 1/2008 |
| WO | WO 2012/014732 | A1 | 2/2012 |
| WO | WO 2013/067271 | A2 | 5/2013 |
| WO | WO 2013/142249 | A1 | 9/2013 |

OTHER PUBLICATIONS

Philip Haw, The HLB System, Mar. 9, 2004, www.uniqema.com, full document.*

Kelly Dobos, Chemists Corner, HLB—The Easiest Way to Create an Emulsion, http://chemistscorner.com/hlb-the-easiest-way-to-create-an-emulsion/, full document.*

Abstract and Machine Translation of JP2000128773, May 9, 2000, 7 pages.

International Search Report and Written Opinion for PCT/US2015/015318 dated May 18, 2015, 8 pages.

Evonik Industries, "Isolan GPS-Emulsifier for low fiscous W/O lotions", http://glenncorp.com/wp-content/uploads/2013/11/DS_ISOLAN_GPS_e.pdf, accessed Jul. 3, 2017, 5 pages.

* cited by examiner

SPRAY DELIVERY DEVICE

RELATED APPLICATION

The present application claims priority to U.S. Provisional Application Ser. No. 61/939,830, filed on Feb. 14, 2014, which is incorporated herein in its entirety by reference thereto.

BACKGROUND OF THE INVENTION

Much of the population has experienced a skin condition such as a rash, a pressure ulcer, a wound such as a cut or first degree burn, an allergic reaction, or any other skin condition that can cause itching, inflammation, pain, or any other type of discomfort that has required topical application of a cream or ointment to assist in the healing process. Often, some of these conditions are more prevalent in infants, the elderly, and infirm. For instance, infants, the elderly, and infirm can be susceptible to developing incontinent dermatitis, which occurs when the skin is exposed to prolonged wetness, increased skin pH caused due to contact with urine and feces, and the resulting breakdown of the stratum corneum, or the outermost layer of the skin. Meanwhile, pressure ulcers, also known as decubitus ulcers or bedsores, are also a concern. Pressure ulcers are localized injuries to the skin and/or underlying tissue that usually occur over a bony prominence as a result of pressure, or pressure in combination with shear and/or friction. The most common sites are the sacrum, coccyx, heels or the hips, but other sites such as the elbows, knees, ankles or the back of the cranium can be affected. Pressure ulcers occur due to pressure applied to soft tissue resulting in completely or partially obstructed blood flow to the soft tissue. Factors that can contribute to the formation of ulcers include protein-calorie malnutrition, microclimate (skin wetness caused by sweating or incontinence), diseases that reduce blood flow to the skin, such as arteriosclerosis, or diseases that reduce the sensation in the skin, such as paralysis or neuropathy.

The aforementioned conditions, and other skin conditions, can be prevented or treated, for instance, by the application of an active agent to the affected area of the skin. Active agents can, for instance, help speed up the wound healing process and can also limit the skin's exposure to excessive moisture. As such, one approach for treating these skin conditions is to block moisture from reaching the skin, such as by the application of oil-based protectants or barrier creams, such as various over-the-counter creams or ointments containing moisture barrier active agent particles, to the affected area. However, if the skin is not thoroughly dry, some of these oil-based protectants and creams can actually seal the moisture inside the skin rather than outside the skin. Further, such protectants and creams are very viscous and can be greasy, resulting in difficulty in removing the protectants and creams from one's hands after application onto the affected area of the skin. In addition, rubbing these products into the skin can cause additional discomfort or pain, and in the event that a caretaker or healthcare provider must apply the product to a patient, this could lead to embarrassment for both the patient and caretaker depending on the location of application.

As such, a need exists for a composition that can provide an even coating of an active agent to the skin that is easier to apply and that does not cause discomfort. One approach is to use an active agent in conjunction with a propellant to create a sprayable composition. However, often the high viscosity of the resulting aerosol spray composition means that it can be difficult to formulate the composition into a medium that can be sprayed due to issues with clogging of active agent particles in the valves and nozzle in the dispenser. Meanwhile, to counteract this problem, other sprayable compositions are formulated to have a low viscosity to allow for spraying, but this can result in compositions that are not viscous enough when applied to the skin's surface, resulting in a runny product that does not evenly coat or effectively contact the skin.

Still another problem associated with the aforementioned sprays is that the active agents of the sprayable compositions are particulate-based and often settle to the bottom of the container in which the e composition is stored, particularly when the viscosity is low, resulting in caking of the active agent in the container and the inability to deliver the active agent in a uniform manner.

As such, a need exists for a stable, sprayable composition containing active agent particles that remain substantially homogeneously distributed and that can be evenly sprayed onto the skin as a fine mist without clogging.

SUMMARY OF THE INVENTION

In accordance with one embodiment of the present invention, a spray delivery system is disclosed. The system includes an active agent composition and a container. The active agent composition has a viscosity ranging from about 500 centipoise to about 10,000 centipoise and includes a hydrofluoro-based propellant, a carrier fluid, and active agent particles. Meanwhile, the container includes a dip tube; a valve assembly comprising a valve body, a stem comprising a stem orifice, and a vapor tap; and an actuator, where the dip tube is coupled to the actuator by the valve assembly. The actuator is depressed to dispense the active agent composition stored in the container.

Other features and aspects of the present invention are set forth in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figure, in which.

Figure 1:
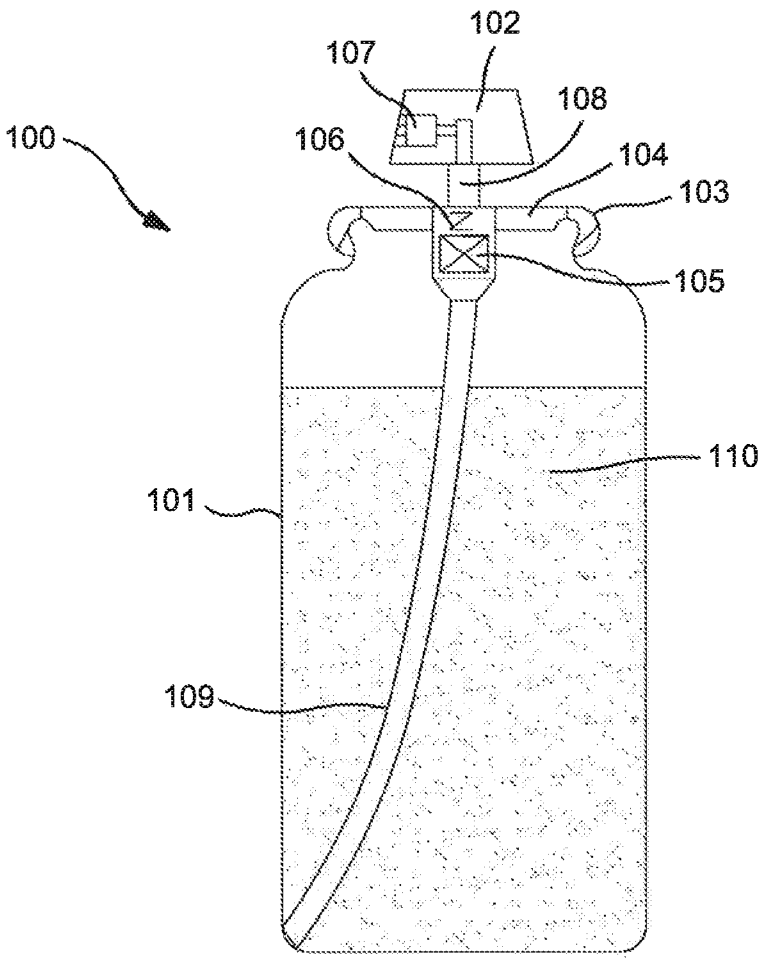
FIG. 1 is a cross-sectional side view of a spray delivery system according to one embodiment of the present disclosure.

Repeat use of reference characters in the present specification and drawing is intended to represent the same or analogous features or elements of the present invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention.

Generally speaking, the present invention is directed to a spray delivery system that can be used, for example, in the treatment of a skin condition or any other condition where the topical application of an active agent is desired. The spray delivery system includes a sprayable active agent composition housed within a container. The sprayable active agent composition includes a hydrofluoro-based propellant, a carrier fluid, and active agent particles and has a viscosity ranging from about 500 centipoise to about 10,000 centipoise. The container includes a dip tube; a valve assembly that includes a valve body, a stem comprising a stem orifice, and a vapor tap; and an actuator. The dip tube is coupled to the actuator by the valve assembly, and the actuator is depressed to dispense the sprayable active agent composition. By selectively controlling the components used in and the viscosity of the composition, as well the arrangement and dimensions of the container components, the active agent particles resist settling so a substantially homogeneous distribution of the particles is maintained. Thus, the composition can be stable and evenly dispensed from the container as a fine mist without clogging. For instance, the spray delivery system includes a sprayable active agent composition that can be stable such that less than about 3 wt. %, such as less than about 2 wt. %, such as less than about 1 wt. % of the active agent particles in the composition settle when stored in a container at 21° C. for 3 days. This results in a composition that can be evenly sprayed on a surface as a substantially uniform coating of active agent particles.

First, the components of the container used in the spray delivery system are selected to prevent clogging of the sprayable active agent composition and promote an even spray. For instance, the actuator that is depressed in order to dispense the composition from the container can have an exit orifice that has a diameter ranging from about 0.3 millimeters to about 0.6 millimeters, such as from about 0.35 millimeters to about 0.55 millimeters, such as from about 0.4 millimeters to about 0.5 millimeters to prevent clogging of the exit orifice with active agent particles. Additionally, the actuator can be a non-mechanical breakup actuator, as mechanical breakup actuators include channels that are prone to clogging when used in conjunction with spray compositions containing particles. Further, the stem orifice component of the container can have a diameter ranging from about 0.5 millimeters to about 0.75 millimeters, such as from about 0.55 millimeters to about 0.7 millimeters, such as from about 0.6 millimeters to about 0.65 millimeters, which can also prevent clogging as the active agent particles pass from the dip tube up through the stem orifice.

Meanwhile, the diameter of the vapor tap, which is used to promote mixing of the propellant, carrier fluid, and active agent particles in the composition in the valve body, can range from about 0.1 millimeters to about 0.5 millimeters, such as from about 0.15 millimeters to about 0.45 millimeters, such as from about 0.2 millimeters to about 0.4 millimeters. This results in a substantially homogeneous distribution of the propellant and active agent particles throughout the sprayable composition in the valve body. Such a distribution prevents clogging in the valve body and actuator and allows for an even spray from the exit orifice.

Further, the components in the sprayable active agent composition component of the spray delivery system can be selectively controlled to provide for a spray delivery system that resists clogging and provides an even spray. For instance, based on the nature and type of components selected, the viscosity of the composition can range from about 500 centipoise to about 10,000 centipoise, such as from about 1000 centipoise to about 8000 centipoise, such as from about 1500 centipoise to about 6000 centipoise, such as from about 2000 centipoise to about 4000 centipoise, which results is an composition that is not so thick that it clogs the spray delivery system but is not so runny that the resulting spray cannot be uniformly coated onto a surface.

Turning now to the specific components in the composition utilized in the spray delivery system, a hydrofluoro-based propellant can be used in conjunction with a base active agent composition that includes active agent particles and a carrier fluid. The ratio of the specific gravity of the propellant to the specific gravity of the overall composition can be selected to range from about 0.7 to about 1.6, such as from about 0.8 to about 1.5, such as from about 0.9 to about 1.4. Such a specific gravity ratio results in the propellant having a specific gravity similar to the overall composition, which means that the propellant can be substantially homogeneously distributed throughout the composition. Because the propellant is distributed throughout the composition in this manner, settling of the active agent particles in the composition can be prevented, which contributes to the ability of the spray delivery system to resist clogging and to deliver an even spray on a surface.

The various components of the spray delivery system are discussed in more detail below.

I. Sprayable Active Agent Composition a. Propellant

The spray delivery system of the present invention includes a sprayable active agent composition that includes a propellant to provide the energy needed to aid in the delivery of active agent particles to a surface of the skin affected with skin conditions such as rashes, ulcers, cuts, or wounds. In other words, the propellant can provide the propulsive forced needed to spray the active agent particles onto the skin. As such, the propellant has enough dispersive energy to overcome the surface tension of the liquid components of the composition.

As stated above, the composition includes a propellant particularly useful for facilitating the spray of the active agent particles. The present inventors have found that by selectively controlling certain aspects of the propellant, such as the specific gravity, vapor pressure, and/or molecular weight, a composition having a substantially homogeneous distribution of active agent particles can be achieved.

The ratio of the specific gravity of the propellant to specific gravity of the sprayable composition can range from about 0.7 to about 1.6, such as from about 0.8 to about 1.5, such as from about 0.9 to about 1.4. Such a specific gravity ratio results in the propellant having a specific gravity similar to the overall composition, which means that the propellant can be substantially homogeneously distributed throughout the composition. Because the propellant is distributed throughout the composition in this manner, settling of the active agent particles and other particulates contained in the composition can be prevented. Further, the propellant can have a specific gravity ranging from about 1.03 to about 1.3, such as from about 1.05 to about 1.25, such as from about 1.07 to about 1.2 as determined at 21° C. and based on water having a density of 1.0 at 21° C. Meanwhile, the sprayable composition can have a specific gravity of from about 0.8 to about 1.3, such as from about 0.85 to about 1.25, such as from about 0.9 to about 1.2, as determined at 21° C.

In addition, the propellant can provide a high enough vapor pressure to the composition such that it can be atomized and sprayed in aerosol form, yet the vapor pressure is not so high that the resulting spray creates excessive misting or discomfort when sprayed onto the skin or requires a specially designed aerosol container. For instance, the vapor pressure at room temperature (21° C.) can be less than about 60 psi. In some embodiments, for example, the vapor pressure can range from about 30 psi to about 60 psi, such as from about 35 psi to about 55 psi, such as from about 40 psi to about 50 psi. Without intending to be limited by theory, it is believed that by using a propellant that has a lower vapor pressure at room temperature compared to other propellants, the propellant can be used in larger amounts in the sprayable composition, which results in a smoother, more easily controlled spray and also ensures complete evacuation of the container in which the sprayable composition is stored. Further, because the propellant's low vapor pressure, it is not necessary to use a high pressure aerosol container as is required when utilizing other propellants.

In addition, the molecular weight of the propellant can be greater than 100 grams per mole, such as from about 100 grams per mole to about 400 grams per mole, such as from about 105 grams per mole to about 300 grams per mole, such as from about 110 grams per mole to about 200 grams per mole. By using a propellant having a molecular weight in this range, settling of the active agent particles can be further prevented.

In one embodiment, the propellant can include at least one hydrofluoro-olefin. In one particular embodiment, the propellant includes a hydrofluoro-olefin containing from 3 to 4 carbon atoms, such as three carbon atoms. The hydrofluoro-olefin propellant of the present invention can be referred to as an "HFO" when it contains at least one hydrogen, at least one fluorine and no chlorine. HFOs are derivatives of alkenes. In some embodiments, the HFO propellant can contain two carbon-carbon double bonds.

In one particular embodiment, the sprayable active agent composition of the present invention includes a propellant represented by Formula I below:

(Formula I)

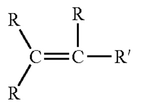

where each R is independently a hydrogen or a halogen such as fluorine (F), bromine (Br), iodine (I), or chlorine (Cl), and preferably fluorine (F), R' is $(CR_2)_nY$, Y is $CRF_2$, and n is 0 or 1.

Further, in one particular embodiment, Y is $CF_3$, n is 0, and at least one of the remaining Rs is F. In another particular embodiment, Y is $CF_3$, at least one R on the unsaturated terminal carbon is H, and at least one of the remaining Rs is F. In still other embodiments, the fluoro-olefin propellant of the present invention can include one or more tetrafluoropropenes, and such a propellant can be referred to herein as a HFO-1234 propellant. Examples of tetrafluoropropenes contemplated by the present invention are HF1234yf (specific gravity of 1.092 at 21° C.) and HF0-1234ze (specific gravity of 1.17 at 21° C.), in the cis- and/or trans-forms. It should be understood that HFO-1234ze refers to 1,1,1,3-tetrafluoropropene, independent of whether it is the cis- or trans-form, and the terms "cisHFO-1234ze" and "transHFO-1234ze" are used herein to describe the cis- and trans-forms of 1,1,1,3-tetrafluoropropene, respectively. In some embodiments, the HFO-1234ze can include a combination of transHFO-1234ze and cisHFO-1234ze, such as from about 90% to about 99% trans-isomer on the basis of total HFO-1234ze, with the cis-isomer comprising from about 1% to about 10% of the same basis. As such, in some embodiments, the propellant of the present invention can include a combination of cisHFO-1234ze and transHFO-1234ze, preferably in a cis- to trans-weight ratio of from about 1:99 to about 10:99, such as from about 1:99 to about 5:95, such as from about 1:99 to about 3:97.

Although the properties of cisHFO-1234ze and transHFO-1234ze differ in at least some respects, it is contemplated that each of these compounds is adaptable for use, either alone or together with other compounds including its stereoisomer, as a propellant in the sprayable composition of the present invention. For example, while transHFO-1234ze has a relatively low boiling point (−19° C.), it is nevertheless contemplated that cisHFO-1234ze, with a boiling point of 9° C., can also be used as a propellant in the sprayable composition of the present invention. Further, it is to be understood that the terms HFO-1234ze and 1,1,1,3-tetrafluoropropene refer to both stereo isomers, and the use of these terms covers both the cis- and trans-forms. Another type of propellant that can be used is a hydrofluoroalkane, which can be referred to as an "HFA." HFA propellants are also known as hydrofluorocarbons or "HFC" propellants. An example of a suitable HFC propellant is 1,1,1,2-tetrafluoroethane, which can also be referred to as HFC-134a. Another type of HFC propellant that can be used is 1,1,1,2,3,3,3-heptafluoropropane, which can also be referred to as HFC-227ea.

Regardless of the particular propellant utilized, the amount of the propellant contained in the sprayable active agent composition of the present invention can range from about 5 wt. % to about 95 wt. %, such as from 10 wt. % to about 80 wt. %, such as from about 15 wt. % to about 60 wt. % based on the total weight of the composition.

b. Active Agent Particles

The sprayable composition of the present invention further includes active agent particles, which can mean any compound or mixture of compounds which produces a physiological result upon contact with a living organism (e.g., a mammal) such as a human. Active agent particles can be distinguishable from other components of the sprayable composition such as preservatives, conditioning agents, emollients, viscosity modifiers, emulsifiers, etc. The active agent particles can include any molecule, as well as a binding portion or fragment thereof, that is capable of modulating a biological process. In some embodiments, the active agent particles can be used in the diagnosis, treatment, or prevention of a disease or as a component of a medication, pharmaceutical, cosmetic, or cosmeceutical. Further, the active agent particles can be compounds that interact with or influence or otherwise modulate a target in a living subject. The target may be a number of different types of naturally occurring structures, where targets of interest include both intracellular and extra-cellular targets. Active agent particles can include, for example, moisture barriers, antifungals, antibacterials, analgesics, antiseptics, anesthetics, anti-inflammatories, antipruritics, etc. The active agent particles can have an average particle size of from about 20 nanometers to about 1000 nanometers, such as from about 25 nanometers to about 500 nanometers, such as from about 30 nanometers to about 250 nanometers.

In one embodiment, the active agent particles can include zinc oxide particles, which repel moisture and create a barrier between the skin and environment to protect the skin from excessive moisture. The zinc oxide particles can have an average particle size of from about 20 nanometers to about 200 nanometers, such as from about 25 nanometers to about 150 nanometers, such as from about 30 nanometers to about 100 nanometers.

The zinc oxide particles can be hydrophobic, for example, by application of a hydrophobic coating on the surface of the zinc oxide particles, as described in more detail below. The particles can also carry an inorganic coating, separately or in combination with the hydrophobic coating, as described in more detail below. The zinc oxide particles may be coated with alumina, silica, an organic material, silicones, or combinations thereof. Other suitable surface treatments may include: phosphate esters (including lecithins), perfluoroalkyl alcohol phosphates, fluorosilanes, isopropyl titanium triisostearate, stearic or other fatty acids, silanes, dimethicone and related silicone polymers, or combinations thereof.

For example, zinc oxide particles may be coated with oxides of other elements such as oxides of aluminum, zirconium or silicon, or mixtures thereof such as alumina and silica. Alternatively, the zinc oxide particles may be treated with boron nitride or other known inorganic coatings, singly or in combinations before incorporation into the voids of the particulate. The inorganic coating may be applied using techniques known in the art. A typical process can include forming an aqueous dispersion of zinc oxide particles in the presence of a soluble salt of the inorganic element whose oxide will form the coating. This dispersion is usually acidic or basic, depending upon the nature of the salt chosen, and precipitation of the inorganic oxide is achieved by adjusting the pH of the dispersion by the addition of acid or alkali, as appropriate. The inorganic coating, if present, can be applied as a first layer to the surface of the zinc oxide particles.

In another embodiment, the zinc oxide particles can include an organic coating that provides hydrophobicity. The organic coating can be applied to the inorganic coating, if present, or directly to the zinc oxide. The hydrophobic coating agent may be, for example, a silicone, a silane, a metal soap, a titanate, an organic wax, or combinations thereof. The hydrophobic coating can alternatively include a fatty acid, for example, a fatty acid containing 10 to 20 carbon atoms, such as lauric acid, stearic acid, isostearic acid, and salts of these fatty acids. The fatty acid may be isopropyl titanium trisostearate. With respect to the silicone, the hydrophobic coating may be a methicone, a dimethicone, their copolymers or mixtures thereof. The silicone may also be an organosilicon compound, for example dimethylpolysiloxanes having a backbone of repeating —$Me_2SiO$— units ("Me" is methyl, $CH_3$), methyl hydrogen polysiloxanes having a backbone of repeating —MeHSiO— units and alkoxysilanes of formula $R_nOSiH_{(4-n)}$where "R" is alkyl and "n" is the integer 1, 2 or 3. With respect to the silane, the hydrophobic coating agent may be an alkoxysilanes, for example an alkyltriethoxy or an alkyltrimethoxy silanes available from OSI Specialties or PCR. The alkoxysilane may be a triethoxycaprylylsilane or a perfluoroalkylethyl triethoxysilane having a $C_3$ to $C_{12}$ alkyl group that is straight or branched. Zinc oxide particles with a triethoxycaprylylsilane coating are commercially available under the name ZANO™ 10 Plus from Umicore Zinc Chemicals.

Still other active agent particles that can be used in the sprayable composition can include paraffin, microcrystalline wax, petrolatum, beeswax, or a combination thereof. Such active agent particles can act as moisture repellant materials.

Regardless of the type of active agent particles utilized, the amount of active agent particles contained in the sprayable composition of the present invention can range from about 0.1 wt. % to about 30 wt. %, such as from 1 wt. % to about 25 wt. %, such as from about 2 wt. % to about 20 wt. % based on the total weight of the composition.

c. Carrier Fluid

The sprayable active agent composition can also include a carrier fluid in which the propellant and active agent particles can be substantially homogeneously dispersed. In some embodiments, the carrier fluid can include an oil phase and a water phase. The oil phase and the water phase can form a water-in-oil emulsion or an oil-in-water emulsion. In other embodiments, the carrier fluid can be oil or water.

Suitable oils that can be used in the carrier fluid include mineral oils, plant-based oils, silicone oils, or a combination thereof. Examples of commercially available mineral oils, which are liquid petroleum derivatives that may be used in accordance with the present invention can include Witco Corporation's CARNATION™ mineral oil or Penreco Corporation's DRAKEOL™ mineral oil. Suitable plant-based oils, which are non-petroleum biomass derived oils, that can be used include vegetable or fruit oils, such as almond oil, peanut oil, wheat germ oil, linseed oil, jojoba oil, apricot pit oil, walnut oil, palm nut oil, pistachio nut oil, sesame seed oil, rapeseed oil, cade oil, corn oil, peach pit oil, poppy seed oil, pine oil, castor oil, soybean oil, avocado oil, safflower oil, coconut oil, hazelnut oil, olive oil, grape seed oil, sunflower oil, apricot kernel oil, geranium oil, rice bran oil and mixtures thereof. Silicone oils that can be used include disiloxane, cyclomethicone, dimethicone and derivatives thereof, and polydimethylsiloxane fluids. Cyclomethicone is a volatile compound and evaporates when applied to the skin's surface, such that the resulting coating is drier to the touch. Other similar volatile compounds that can be used include isododecane.

Water can also be used as a carrier fluid either alone or in conjunction with any of the oils described above in a water-in-oil emulsion or an oil-in-water emulsion. It is of course not intended that the carrier fluid be limited to the materials described above. When the carrier fluid includes both oil and water, the oil can be present in the emulsion in an amount ranging from about 1 wt. % to about 35 wt. %, such as from about 3 wt. % to about 30 wt. %, such as from about 5 wt. % to about 25 wt. % based on the total weight of the composition. Meanwhile, the water can be present in an amount less than about 50 wt. %, such as an amount ranging from about 1 wt. % to about 50 wt. %, such as from about 5 wt % to about 45 wt. %, such as from about 10 wt. % to about 40 wt. % based on the total weight of the composition. Further, the total amount of carrier fluids present in the composition can range from about 10 wt. % to about 70 wt. %, such as from about 15 wt. % to about 65 wt. %, such as from about 20 wt. % to about 60 wt. % based on the total weight of the composition.

d. Emulsification System

The sprayable composition can also include an emulsification system. The emulsification system can include one or more emulsifiers to help create a stable, substantially homogeneous, uniform dispersion of the propellant and the active agent particles by preventing the separation of the sprayable composition into constituent phases. The emulsification system may include one or more nonionic, anionic, and/or amphoteric emulsifiers, including mixtures containing different species or mixtures of different surfactants within the same species. In one particular embodiment, the emulsification system includes one or more nonionic emulsifiers.

Nonionic surfactants, which typically have a hydrophobic base (e.g., long chain alkyl group or an alkylated aryl group) and a hydrophilic chain (e.g., chain containing ethoxy and/or propoxy moieties), can be particularly suitable. Some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglycerides, or diglycerides of long chain alcohols, and mixtures thereof. Particularly suitable nonionic emulsifiers may include ethylene oxide condensates of fatty alcohols (e.g., sold under the trade name Lubrol), polyoxyethylene ethers of fatty acids (particularly $C_{12}$-$C_{20}$ fatty acids), polyoxyethylene sorbitan fatty acid esters (e.g., sold under the trade name TWEEN®), and sorbitan fatty acid esters (e.g., sold under the trade name SPAN™ or ARLACEL®), etc. The fatty components used to form such emulsifiers may be saturated or unsaturated, substituted or unsubstituted, and may contain from 6 to 22 carbon atoms, in some embodiments from 8 to 18 carbon atoms, and in some embodiments, from 12 to 14 carbon atoms.

Although any emulsifier may generally be employed, the present inventors have discovered that a certain combination of hydrophilic and lipophilic nonionic emulsifiers is particularly effective in stabilizing the sprayable composition. As is known in the art, the relative hydrophilicity or lipophilicity of an emulsifier can be characterized by the hydrophilic/lipophilic balance ("HLB") scale, which measures the balance between the hydrophilic and lipophilic solution tendencies of a compound. The HLB scale ranges from 0.5 to approximately 20, with the lower numbers representing highly lipophilic tendencies and the higher numbers representing highly hydrophilic tendencies. Desirably, the sprayable composition can include at least one "hydrophilic" emulsifier that has an HLB value of from about 10 to about 20, in some embodiments from about 12 to about 19, and in some embodiments, from about 14 to about 18. Likewise, the sprayable composition can also include at least one "lipophilic" emulsifier that has an HLB value of from about 0.5 to about 10, in some embodiments from about 1 to about 9, and in some embodiments, from about 2 to about 8. If desired, two or more surfactants may be employed that have HLB values either below or above the desired value, but together have an average HLB value within the desired range. Regardless, the present inventors have discovered that the weight ratio of lipophilic emulsifiers to hydrophilic emulsifiers in the sprayable composition can typically be within a range of from about 5 to about 30, in some embodiments from about 7.5 to about 25, and in some embodiments, from about 10 to about 20. Further, the present inventors have discovered that the overall HLB value of the sprayable composition is generally lipophilic and can range from about 2 to about 12, such as from about 3 to about 10, such as from about 4 to about 9, such as from about 5 to about 8.

One particularly useful group of "lipophilic" emulsifiers are sorbitan fatty acid esters (e.g., monoesters, diester, triesters, etc.) prepared by the dehydration of sorbitol to give 1,4-sorbitan, which is then reacted with one or more equivalents of a fatty acid. The fatty-acid substituted moiety can be further reacted with ethylene oxide to give a second group of surfactants. The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,g-sorbitan sesquiester or 1,4-sorbitan triester. The common names for these surfactants include, for example, sorbitan monolaurate, sorbitan monopalmitate, sorbitan monoestearate, sorbitan monooleate, sorbitan sesquioleate, and sorbitan trioleate. Such surfactants are commercially available under the name SPAN™ or ARLACEL™, usually with a letter or number designation which distinguishes between the various mono-, di- and triester substituted sorbitans. SPAN™ and ARLACEL™ surfactants are lipophilic and are generally soluble or dispersible in oil, but not generally soluble in water. One particularly suitable surfactant is sorbitan oleate, which is commercially available as SPAN™ 80. Generally these surfactants will have HLB value in the range of 1.8 to 8.6.

Other useful lipophilic emulsifiers that can be used can include, for example, silicone water-in-oil emulsifiers. By silicone it is meant a molecule that includes at least one siloxane (—Si—O—) repeating unit and further includes a hydrophobic moiety and a hydrophilic moiety. The HLB value of the silicone water-in-oil emulsifier is relatively low. For example, in some embodiments, the silicone emulsifier can have an HLB value in the range of 2 to 9.

Examples of suitable silicone water-in-oil emulsifiers can include non-crosslinked dimethicone copolyols such as alkoxy dimethicone copolyols, silicones having pendant hydrophilic moieties such as linear silicones having pendant polyether groups, branched polyether and alkyl modified silicones, branched polyglycerin and alkyl modified silicones, and combinations thereof. Examples of commercially available non-crosslinked dimethicone copolyols include the following from Dow Corning of Midland, Mich.: cyclopentasiloxane and PEG/PPG-18/18 dimethicone available as DC 5225C, and cyclopentasiloxane and PEG-12 dimethicone crosspolymer available as DC9011. Certain non-crosslinked dimethicone copolyols are cetyl dimethicone copolyols such as cetyl PEG/PPG-10/1 dimethicone sold under the name ABIL™ EM-90, branched polyether and alkyl modified silicones such as lauryl PEG-9 polydimethylsiloxyethyl dimethicone sold under the name KF-6038, and branched polyglycerin and alkyl modified silicones such as lauryl polyglyceryl-3 polydimethylsiloxyethyl dimethicone sold under the name KF-6105. Other non-crosslinked dimethicone copolyols include, for example, bis-PEG/PPG-14/dimethicone copolyol sold under the name ABIL™ EM-97 and the polyglyceryl-4 isostearate/cetyl dimethicone copolyol/hexyl laurate mixture sold under the name ABIL™ WE 09. ABIL™ EM-90, ABIL™ EM-97, and ABIL™ WE 09 are available from Evonik Goldschmidt GmbH of Essen, Germany, KF-6038 are KF-6105 are available from Shin-Etsu Silicones of Akron, Ohio. One particularly suitable emulsifier for use in the present invention is ABIL™ WE 09, which has an HLB value of about 5. Another particularly suitable emulsifier is ABIL™ EM 90, which also has an HLB value of about 5. Still another suitable nonionic lipophilic emulsifier that can be included in the sprayable active agent composition of the present invention is octyldodecanol/octyldechyl xyloside/PEG-30, which is commercially available from Seppic S.A. under the name EASYNOV™.

Meanwhile, sorbitan fatty acid esters (e.g., monoesters, diester, triesters, etc.) that have been modified with polyoxyethylene are likewise a particularly useful group of "hydrophilic" emulsifiers. These materials are typically prepared through the addition of ethylene oxide to a 1,4-sorbitan ester. The addition of polyoxyethylene converts the lipophilic sorbitan ester surfactant to a hydrophilic surfactant that is generally soluble or dispersible in water. Such materials are commercially available under the designation TWEEN™ (e.g., TWEEN™ 80, polysorbate 80, or polyethylene (20) sorbitan monooleate). TWEEN™ surfactants generally have a HLB value in the range of 9.6 to 16.7. For instance TWEEN™ 80 has an HLB value of 15. Still other suitable hydrophilic emulsifiers can include sucrose fatty acid esters, such as saccharose monopalmitate (HLB of 15) and saccharose monostearate (HLB of 11), or PEG-32 glyceryl laurate (HLB of 14), as well as polyethylene glycol (PEG) n-alkanol esters of the BRIJ™ family such as BRIJ™ 35, 56, 58, 76, 78, and 99, which have an HLB in the range of 12.4 to 16.9. BRIJ™ 56 is polyoxyethylene[10] cetyl ether, for example, has an HLB value of 12.9.

Regardless of the particular emulsifiers utilized in the emulsification system, the emulsification system can be present in the sprayable composition in an amount ranging from about 0.1 wt. % to about 20 wt. %, such as from about 0.5 wt. % to about 15 wt. %, such as from about 1 wt. % to about 10 wt. % based on the total weight of the composition. Further, the present inventors have discovered that the weight ratio of lipophilic emulsifiers to hydrophilic emulsifiers in the emulsification system component of the sprayable composition is typically within a range of from about 5 to about 30, in some embodiments from about 7.5 to about 25, and in some embodiments, from about 10 to about 20.

e. Viscosity Modifier

In addition, the sprayable composition can include one or more viscosity modifiers which can also help to prevent the separation of the various components of the composition. For instance, in some embodiments, such as when the carrier fluid includes more than one component, one or more viscosity modifiers can be added to the oil phase or the water phase of an emulsion to adjust the viscosity such that separate components in the composition are more miscible. Further, the viscosity of the overall active agent composition can be adjusted so that it is not so high that the composition cannot be sprayed onto a surface, but it is not so low that the composition is too runny such that it does not evenly coat the surface. As such, the composition can have a viscosity ranging from about 500 centipoise to about 10,000 centipoise, such as from about 1000 centipoise to about 8000 centipoise, such as from about 1500 centipoise to about 6000 centipoise, such as from about 2000 centipoise to about 4000 centipoise.

When a water-in-oil emulsion or an oil-in-water emulsion is formed, the one or more viscosity modifiers can be added to the water phase of the water-in-oil emulsion or the oil-in-water emulsion to enhance the miscibility between the water phase and the oil phase, which promotes the substantially homogeneous distribution of the components of the sprayable composition. It is also to be understood, however, that the viscosity modifier can be added to an already-formed oil-in-water or water-in-oil emulsion to adjust the viscosity as needed.

Suitable viscosity modifiers include carboxylic acid polymers which are crosslinked compounds containing one or more monomers derived from acrylic acid, substituted acrylic acids, and salts and derivatives of these acrylic acids and substituted acrylic acids. They can be crosslinked homopolymers of an acrylic acid or of a derivative thereof, such as acrylamidopropylsulfonic acid. They can be also crosslinked copolymers having (i) a first monomer selected from the group consisting of (meth)acrylic acid, derivatives thereof, short chain (i.e., $C_1$-$C_4$) acrylate ester monomers, and mixtures thereof, and (ii) a second monomer which is a long chain (i.e., $C_8$-$C_{40}$) substituted polyethylene glycol acrylate ester monomer.

Examples of commercially available carboxylic acid polymers include CARBOPOL™ 1342, PEMULEN™ TR-1, and PEMULEN™ TR-2 available from Lubrizol Corp.; Sepigel 305, SIMULGEL™ EG, SIMULGEL™ NS, and SIMULGEL™ 600, available from Seppic S.A.; VISCOLAM™ AT100P and VISCOLAM™ AT64/P, available from Lamberti S.p.A. One commercially available viscosity modifier is available from Seppic S.A. as SIMULGEL™ NS. SIMULGEL™ NS includes a hydroxylethyl acrylate/sodium acryloyldimethyl taurate copolymer, squalane, and polysorbate 60, which can be added to an oil phase of a water-in-oil or oil-in-water emulsion.

Other suitable viscosity modifiers that can be used include cornstarch (topical starch), talc, rice starch, oat starch, tapioca starch, potato starch, legume starches, soy starch, turnip starch, microcrystalline cellulose, kaolin, aluminum starch octenyl succinate, and mixtures thereof. Water soluble aluminum starch octenyl succinates are commercially available from National Starch & Chemical Co. as DRY FLO™ Pure, DRY FLO™ XT, DRY FLO™ PC, and/or DRY FLO™ AF (aluminum free grade) and are water soluble such that they can be included in a water phase of a water-in-oil emulsion or an oil-in-water emulsion.

Regardless of the particular viscosity modifiers utilized, the viscosity modifier can be present in the sprayable composition in an amount ranging from about 0.05 wt. % to about 15 wt. %, such as from about 0.1 wt. % to about 10 wt. %, such as from about 0.5 wt. % to about 5 wt. % based on the total weight of the composition.

f. Conditioning Agents

The sprayable composition can further include one or more conditioning agents to help condition the skin. For example, the sprayable composition can include thymol iodide, sodium chloride, magnesium dichloride, magnesium sulfate, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols, ricinoleate, acetate of ethoxylated alcohols-esters, hydrogenolysis of lanolin, ethoxylated hydrogenated lanolin, ethoxylated sorbitol lanolin, or a combination thereof. Thymol iodide and magnesium sulfate may be particularly useful. One or more conditioning agents can be present in the sprayable composition in an amount ranging from about 0.05 wt. % to about 10 wt. %, such as from about 0.1 wt. % to about 7.5 wt. %, such as from about 0.5 wt. % to about 5 wt. % based on the total weight of the composition.

g. Additional Components

Other optional components in the sprayable composition can include skin care-additives such as emollients, as well as fragrances and preservatives. For instance, an emollient such as caprylic/capric triglyceride can be included in the sprayable composition. Other suitable emollients include stearoxy trimethyl silane, cetyl lactate, and alkyl lactate, such as $C_{12}$-$C_{15}$ alkyl lactate. When emollients are used, the sprayable composition can feel smooth to the touch when applied to the skin. One or more emollients can be present in the sprayable composition in an amount ranging from about 0.1 wt. % to about 25 wt. %, such as from about 0.5 wt. % to about 20 wt. %, such as from about 1 wt. % to about 15 wt. % based on the total weight of the sprayable composition.

Further, a fragrance can be present in the sprayable composition in an amount ranging from about 0.005 wt. % to about 2 wt. %, such as from about 0.01 wt. % to about 1.5 wt. %, such as from about 0.02 wt. % to about 1 wt. % based on the total weight of the sprayable composition.

Meanwhile, preservatives can be present in the sprayable composition in an amount ranging from about 0.01 wt. % to about 6 wt. %, such as from about 0.02 wt. % to about 4 wt. %, such as from about 0.05 wt. % to about 1 wt. % based on the total weight of the composition. Suitable preservatives include paraben-based preservatives such as methylparaben and propylparaben.

In addition, the present inventors have found that a freezing point depressant can be included in the composition to limit the amount of crystallization of any solid components, which can then reduce or limit clogging of the composition when sprayed. If desired, one or more freezing point depressants may be employed, such as glycols (e.g., ethylene glycol, propylene glycol, butylene glycol, triethylene glycol, hexylene glycol, polyethylene glycols, ethoxydiglycol, dipropyleneglycol, etc.); glycol ethers (e.g., methyl glycol ether, ethyl glycol ether, isopropyl glycol ether, etc.); and so forth. Such freezing point depressants can be present in the composition in an amount ranging from about 0.1 wt. % to about 15 wt. %, such as from about 0.5 wt. % to about 10 wt. %, such as from about 1 wt. % to about 5 wt. % based on the total weight of the composition.

II. Formation of the Spray Delivery. System's Active Agent Composition

Generally, the spray delivery system of the present invention can be made by first forming a sprayable active agent composition. The composition can be made by forming a base active agent composition from a carrier fluid and active agent particles, then introducing the base active agent composition into the container component of the spray delivery system, and injecting a propellant into the container. When the base active agent composition is in the form of a water-in-oil emulsion or an oil-in-water emulsion and thus includes a carrier fluid including an oil phase and a water phase, for example, the base active agent composition can be made by first separately forming the oil phase and the water phase.

The manner in which the composition is formed may vary as is known to those skilled in the art. In one embodiment, for example, the oil phase is formed by blending one or more oils with one or more components of the emulsification system described above. However, it is also be understood that one or more of the components of the emulsification system can be added to the water phase in another embodiment. Emollients, conditioning agents, etc. also be added to form the oil phase. In such embodiments, the oil phase can contain oils in an amount of from about 30 wt. % to about 80 wt. %, such as from about 35 wt. % to about 70 wt. %, such as from about 40 wt. % to about 60 wt. % based on the total weight of the oil phase. Further, the oil phase can include emulsifiers in an amount ranging from about 5 wt. % to about 35 wt. %, such as from about 10 wt % to about 30 wt. %, such as from about 15 wt. % to about 25 wt. % based on the total weight of the oil phase. The addition of the emulsifiers can result in an oil phase having an HLB value between about 6 and about 7. In addition, the oil phase can include emollients in an amount ranging from about 10 wt. % to about 45 wt. %, such as from about 15 wt. % to about 40 wt. %, such as from about 20 wt. % to about 35 wt. % based on the total weight of the oil phase. Moreover, the oil phase can include conditioning agents in an amount ranging from about 0.5 wt. % to about 10 wt. %, such as from about 1 wt. % to about 7.5 wt. %, such as from about 1.5 wt. % to about 5 wt. % based on the total weight of the oil phase.

Meanwhile, the water phase can be formed by blending water and any water soluble components of the sprayable composition, such as conditioning agents, viscosity modifiers, emulsifiers, etc. However, it is also to be understood that the water phase may include only water in other embodiments. As such, the water phase can include water in an amount ranging from about 50 wt. % to about 100 wt. %, such as from about 55 wt. % to about 99 wt. %, such as from about 60 wt. % to about 98 wt. %. The water phase can also include conditioning agents in an amount ranging from about 0.5 wt. % to about 15 wt. %, such as from about 1 wt. % to about 10 wt. %, such as from about 1.5 wt. % to about 7.5 wt. % based on the total weight of the water phase. Additionally, the water phase can include viscosity modifiers in an amount ranging from about 0.25 wt. % to about 10 wt. %, such as from about 0.5 wt. % to about 7.5 wt. %, such as from about 1 wt. % to about 5 wt. % based on the total weight of the water phase.

After the oil phase and water phase are separately formed, the water phase can be added to the oil phase to form a water-in-oil emulsion. The combination of the phases may be facilitated through agitation (e.g., stirring) and control of the temperatures of each mixture. Next, the active agent particles can be added to the water-in-oil emulsion. The active agent particles can be present in an amount ranging from about 0.25 wt. % to about 35 wt. %, such as from about 0.5 wt. % to about 30 wt. %, such as from about 1 wt. % to about 25 wt. % based, such as from about 5 wt. % to about 15 wt. % based on the total weight of the base active agent composition.

Then, if desired, other components such as fragrances, preservatives, freezing point depressants, and additional viscosity modifiers can be added to the base active agent composition. Fragrances can be added in an amount ranging from about 0.01 wt. % to about 5 wt. %, such as from about 0.05 wt. % to about 2.5 wt. %, such as from about 0.1 wt. % to about 1 wt. % based on the total weight of the base active agent composition. Likewise, preservatives can be added in an amount ranging from about 0.01 wt. % to about 5 wt. %, such as from about 0.05 wt. % to about 2.5 wt. %, such as from about 0.1 wt. % to about 1 wt. % based on the total weight of the base active agent composition. In addition, freezing point depressants can be added in an amount ranging from about 0.5 wt. % to about 15 wt. %, such as from about 1 wt % to about 10 wt. %, such as from about 2 wt. % to about 8 wt. % based on the total weight of the base active agent composition. Further, viscosity modifiers can be added in an amount ranging from about 0.1 wt. % to about 15 wt. %, such as from about 0.5 wt. % to about 10 wt. %, such as from about 1 wt. % to about 8 wt. % based on the total weight of the base active agent composition. As such, it is to be understood that in some embodiments, a first viscosity modifier can be added during formation of the water phase, while a second viscosity modifier can be added after forming the base active agent by combining the water and oil phases.

Regardless of which phase is being formed, the temperature can range from about 15° C. to about 40° C., such as from about 18° C. to about 35° C., such as from about 20° C. to about 30° C. After the separate phases are mixed as described above, the resulting base active agent composition can then be filled into a spray container, such as an aerosol spray container. The container can then be sealed, after which the propellant can be introduced into the container, such as via a valve. The container can be filled with the propellant at a pressure ranging from about 130 psi to about 230 psi, such as from about 140 psi to about 220 psi, such as from about 150 psi to about 210 psi.

III. Spray Delivery System Container

Various aerosol spray containers can be used in conjunction with the sprayable active agent composition to form the spray delivery system of the present invention, which can be used to spray an active agent composition onto a surface such as skin. One embodiment of a spray delivery system contemplated by the present invention is described with reference to FIG. 1. The spray delivery system 100 can include a spray container 101 formed of metal or reinforced plastic. The spray container 101 has an upper opening into which a spray head 102 is fitted. The spray head or 102 is fixed onto the spray container 101 in such a manner that a flange 104 of the spray head is connected to a collar 103 formed around the edge of the upper opening in the spray container 101 by welding or other possible joining methods. This results in an airtight connection between the spray head 102 and spray container 101.

The spray head 102 is provided with a valve 105 that is retained by the flange 104. The valve 105 is kept closed in its normal condition by the energizing force of a spring 106, but it opens when the spray head 102 is pressed. The spray head 102 further has a spray nozzle 107 which communicates with the valve 105 through a conduit pipe 108. Meanwhile, a dip tube 109 is connected to the valve 105 and extends to the bottom of the spray container 101. By pressing the spray head 102 downwardly against the spring 106, the valve 105 opens to form a fluid passage from the lower end port of the dip tube 109 to the spray nozzle 107 through the valve 105 and conduit pipe 108.

A sprayable composition 110, formed as discussed above, can be charged into the spray container 101. Then, by pressing the spray head 102, the sprayable composition is discharged in the form of a fine mist from the spray nozzle 107 through the aforementioned fluid passage by the pressure associated with the propellant that is substantially homogeneously dispersed in the sprayable composition 110.

Another embodiment of a spray delivery system is described with reference to FIGS. 2A, 2B, 3, and 4. Because of the use of active agent particles, it is possible that the sprayable composition could clog some spray delivery systems. For instance, standard aerosol spray delivery systems often utilize an actuator (spray button) not intended for delivering compositions containing high concentrations of particulate material such as the active agent particles of the present invention. Such actuators often utilize a mechanical break-up insert to finely atomize sprayable compositions containing low levels of particulates. For instance, the actuators can contain small channels to cause a swirling effect, resulting in a fine mist spray. However, when sprayable compositions containing higher amounts of active agent particles are utilized, the active agent particles or any other particles can clog the actuator and prevent an even spray from the container. As such, the spray delivery system of the present invention represented by FIGS. 2A, 2B, 3 and 4 does not include the aforementioned actuator channels and is free from a mechanical breakup insert. Instead, the spray delivery system utilizes a valve and stem system where the stem design allows for automatic wiping of the stem inside the valve as the valve is sprayed, which prevents the buildup of solids inside the valve, thus minimizing the risk of clogging. In addition, the valve includes a valve orifice having a diameter that is large enough such that the active agent particles and other particles of the sprayable composition do not clog inside the container and such that an even mist can be achieved. Further, the valve includes a vapor tap to allow for enhanced blending of the propellant vapor during spraying and to prevent the buildup of particles inside the valve. The addition of the vapor tap also results in a more uniform delivery of the composition from the spray delivery system. Moreover, the vapor tap allows for an increased weight percentage of propellant to be utilized, which helps to create a drier, less runny product when delivered to the surface of the skin. Further, the vapor tap creates a spray that feels warmer because it helps to volatilize the propellant and solvents before the composition reaches the surface of the skin.

Figure 2A:
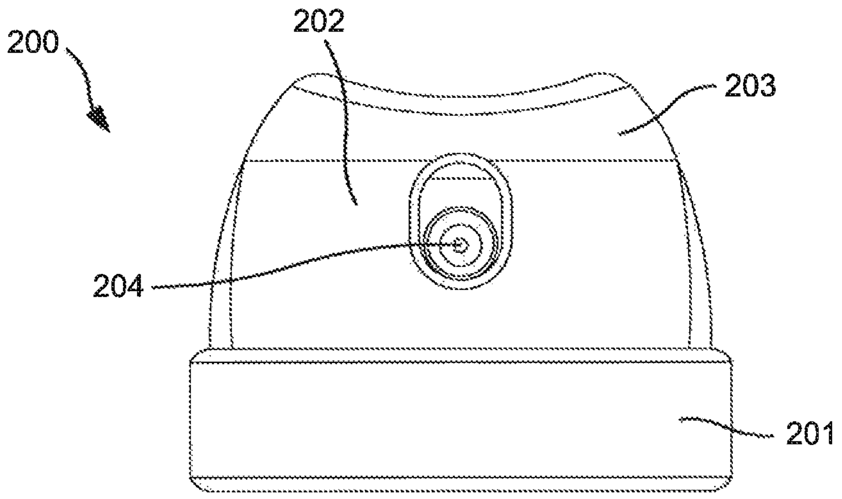
FIG. 2A is front view of an actuator that can be used in a spray delivery system according to one embodiment of the present disclosure.
Figure 2B:
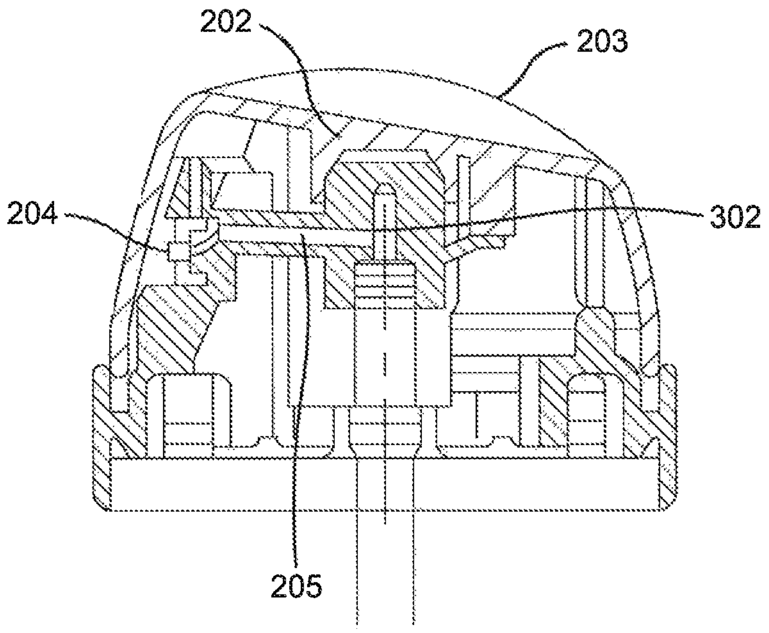
FIG. 2B is a cross-sectional side view of the actuator of FIG. 2A.

The spray system is discussed in more detail below in reference to FIGS. 2A, 2B, 3, and 4. FIG. 2A shows a front view of a non-mechanical breakup actuator 200 that can be used in a spray delivery system according to one embodiment of the present disclosure. The actuator 200 is a component that can be used to depress a stem component of a valve assembly to initiate introduction of the sprayable composition, as is discussed in more detail below in reference to FIGS. 3 and 4. The actuator 200 includes a locking ring 201, an insert 202, and a dome 203. The locking ring 201 keeps the actuator from being depressed inadvertently. The actuator dome 203 can contain the insert 202, and the insert 202 can determine the spray characteristics of the sprayable composition. The insert 202 of FIGS. 2A and 2B is a non-mechanical breakup insert. The insert 202 defines an opening 204 from which the sprayable composition of the present invention can exit the actuator, and the opening is hereinafter referred to as the actuator orifice or exit orifice 204. The exit orifice 204 can have a diameter selected based on the particle size of the particulate components in the sprayable composition, such as the active agent particles, so that the particles and other components of the sprayable composition can be sprayed from the exit orifice 204 without causing clogging of the spray delivery system. Further, by selectively controlling the diameter of the exit orifice 204, the size of the resulting spray pattern can also be influenced. For instance, too small of a diameter can result in a very narrow spray pattern, while too large of a diameter can result in a spray pattern that is too wide, resulting in overspray into the surrounding environment other than the surface to be sprayed, such as clothing, bedding, etc.

For instance, the exit orifice 204 can have a diameter ranging from about 0.3 millimeters to about 0.6 millimeters, such as from about 0.35 millimeters to about 0.55 millimeters, such as from about 0.4 millimeters to about 0.5 millimeters. FIG. 2B is a cross-sectional side view of the actuator of FIG. 2A, which shows the arrangement of the exit orifice 204 in relation to the insert 202 positioned inside the dome 203. The exit orifice is connected to a stem 302 of a valve assembly via an exit path 205, which is discussed in more detail in FIG. 3.

Figure 3:
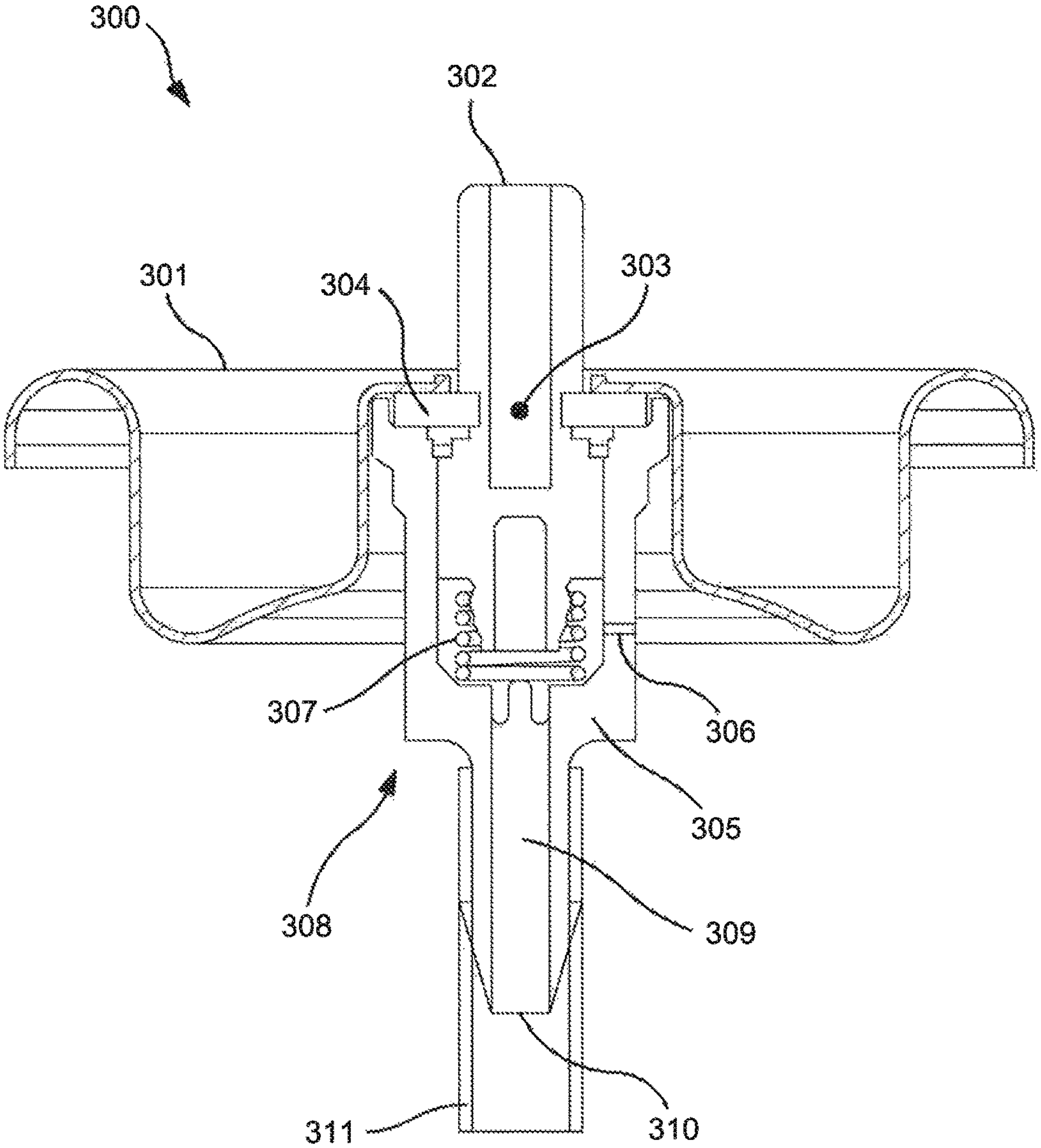
FIG. 3 is a cross-sectional side view of a spray assembly according to one embodiment of the present disclosure.
Figure 4:
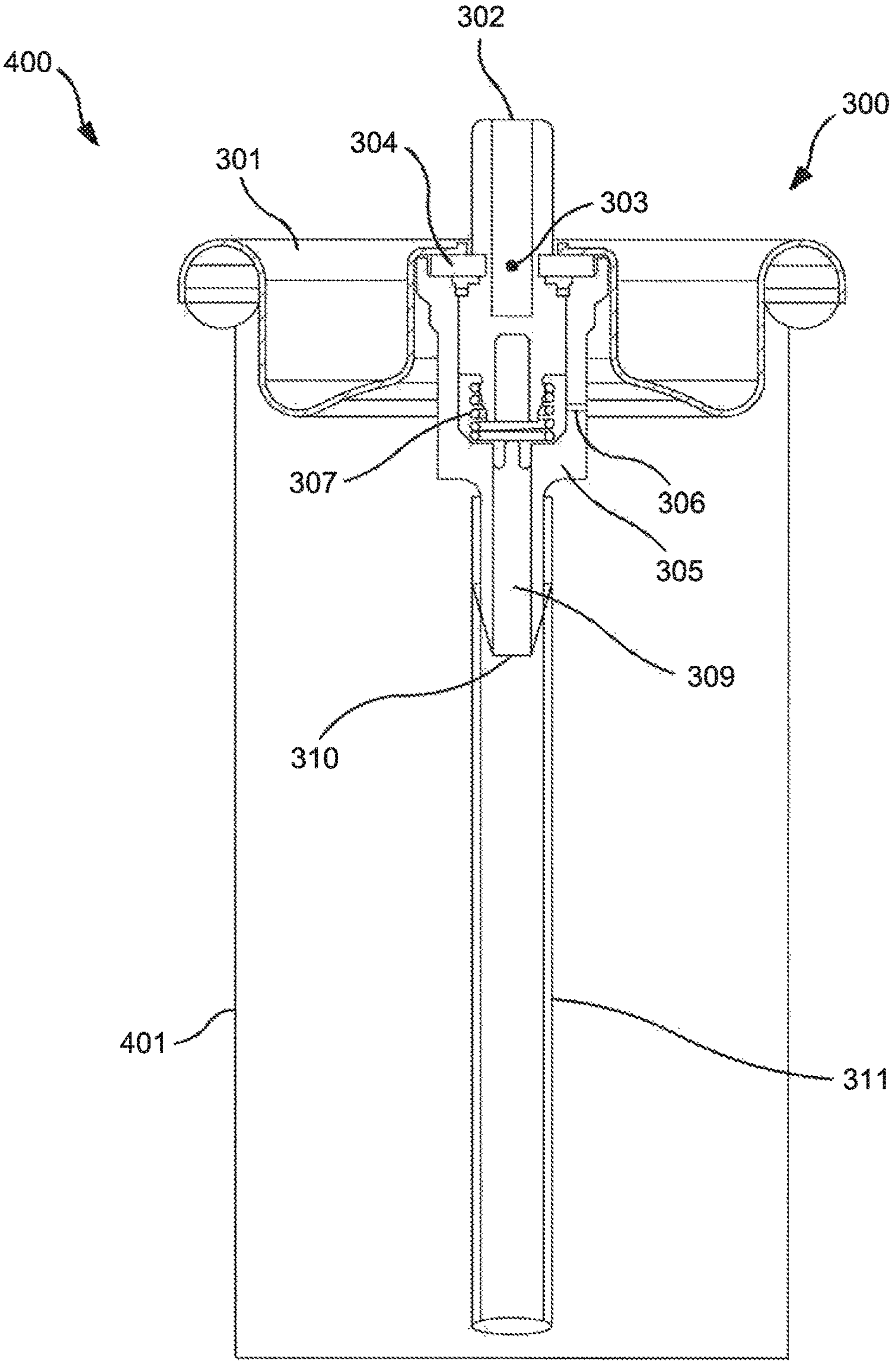
FIG. 4 is a cross-sectional side view of a spray delivery system according to another embodiment of the present disclosure utilizing the spray assembly of FIG. 3.

Turning now to FIGS. 3 and 4, a cross-sectional side view of a spray delivery system that includes a spray valve assembly 300 and mounting cup 301 that can be used in conjunction with the actuator 200 of FIGS. 2A and 2B is shown. The actuator 200 is connected to the valve assembly 300 by exit path 205 as shown in FIG. 2B. The spray valve assembly 300 includes a housing or body 305 that holds the stem 302, a stem gasket 304, and a spring 307. A dip tube 311 is also attached to the housing 305 via a tail pipe 309. The mounting cup 301 holds the spray valve assembly 300 together and can be crimped onto a container 401 to provide a seal. Generally, when the actuator 203 (see FIGS. 2A and 2B), which is disposed above the mounting cup 301, is depressed against the spring 307, the stem 302 of the valve assembly 300 moves downward, opening the seal between the stem gasket 303 and stem 302, such that a stem orifice 303 in the stem 302 passes below the stem gasket 304. This results in the propellant component of the sprayable composition forcing the base active agent composition up the dip tube 311 through a tailpipe orifice 310, into the valve body 305. A vapor tap 306 formed in the valve body 305 supplies additional propellant to the valve body 305 and helps to mix the liquid base active agent composition and propellant in the valve body 305, which can result in a more homogeneous distribution and reduce the risk of clogging of any active agent particles. The vapor tap 306 also keeps the base active agent composition out of the valve body 305 when at rest due to the vapor pushing the base active agent composition down, and also functions to prevent product settling. Once the sprayable composition (i.e., the substantially homogeneously blended propellant and base active agent composition) reaches the stem through the stem orifice 303, it then passes through the exit path 205, and out the exit orifice 204 as a fine mist that does not clog the spray delivery system 400.

The dimensions of the various components can be selected to further minimize the risk of clogging. For instance, the stem 302 can have a diameter of from about 3 millimeters to about 5.5 millimeters, such as from about 3.5 millimeters to about 5 millimeters, such as from about 4 millimeters to about 4.5 millimeters. Meanwhile, the stem orifice 303 can have a diameter of from about 0.5 millimeters to about 0.75 millimeters, such as from about 0.55 millimeters to about 0.7 millimeters, such as from about 0.6 millimeters to about 0.65 millimeters. Additionally, the tailpiece orifice 310 can have a diameter of from about 0.75 millimeters to about 2 millimeters, such as from about 1 millimeter to about 1.75 millimeters, such as from about 1.25 millimeters to about 1.5 millimeters. Further, the vapor tap 306 can have a diameter of from about 0.1 millimeters to about 0.5 millimeters, such as from about 0.15 millimeters to about 0.45 millimeters, such as from about 0.2 millimeters to about 0.4 millimeters. By selectively controlling the aforementioned dimensions, the propellant of the sprayable active agent composition can remain substantially homogeneously distributed throughout the composition to reduce settling of the active agent particles, and the sprayable composition can leave the exit orifice 204 as a fine mist with less fly away and can be more evenly distributed than when, for instance, a mechanical actuator is utilized.

IV. Application of the Sprayable Composition

As a result of the combination of the container components system and the characteristics of the active agent composition used in the spray delivery system, a substantially uniform coating of the composition can be applied to a surface as an even mist that does not clog as it is dispensed form the container. For instance, the composition of the present invention can be applied to a surface of the skin as an even mist and can be used for the treatment of various skin conditions or irritations such as diaper rash; dry skin; ulcers; superficial cuts, scrapes, wounds, and first degree burns; etc. Areas of skin that can be treated include the buttocks, particularly in the case of diaper rash/incontinent dermatitis, as well as the arms, elbows, hands, abdomen, back, sacrum, coccyx, hips, knees, feet, ankles, heels, etc. As the composition reaches the skin's surface, the propellant can evaporate, leaving a substantially uniform coating of the active agent particles on the skin. Further, the active agent particles can be distributed throughout the coating in a substantially uniform manner. After the composition has been sprayed onto the skin in the form of a substantially uniform coating, the amount of active agent particles present in the composition on the skin can range from about 0.25 wt. % to about 35 wt. %, such as from about 0.5 wt. % to about 30 wt. %, such as from about 1 wt. % to about 25 wt. %, such as from about 5 wt % to about 15 wt. % based on the total weight of the resultant coating (e.g., the sprayable composition excluding the evaporated components such as the propellant).

The present invention may be better understood by reference to the following examples.

EXAMPLE 1

A sprayable composition was formed from a base active agent composition including a preservative phase, an oil phase, a water phase, and active agent particles, to which a propellant was added. First, to make the preservative phase of the base active agent composition, a freezing point depressant was added to a beaker and agitated with a propeller. Next, preservatives were added to the beaker and mixing was initiated using a stirrer equipped with an anchor-type sidewipe agitator. Agitation was continued for at least 15 minutes until the solution was completely dissolved. The preservative phase was then set aside.

Next, to make the oil phase of the base active agent composition, emollients were added to a separate beaker and agitated with a propeller to initiate mixing while maintaining a temperature between 20° C. and 23° C., after which the polyglyceryl-4 isostearate/cetyl dimethicone copolyol/hexyl laurate emulsifier was added, followed by the cetyl PEG/PPG-10/1 dimethicone emulsifier, the sorbitan oleate emulsifier, the polysorbate 80 emulsifier, and the octyldodecanol/octyldechyl xyloside/PEG-30 emulsifier. Mixing via agitation was continued, while maintaining a temperature between 20° C. and 25° C. Next, the silicone oil was added to the beaker, while maintaining a temperature between 20° C. and 23° C. A homogenizer was then used for agitation, using cooling water to maintain a temperature between 20° C. and 25° C., after which a conditioning agent was added. Agitation was continued for at least 15 minutes until the solution was completely dissolved, maintaining a temperature between 20° C. and 28° C. The resulting oil phase of the base active agent composition had an HLB value between 6 and 7.

Next, the water phase of the base active agent composition was prepared in a separate beaker. Water was added to the beaker while maintaining a temperature between 20° C. and 28° C. Mixing was initiated using a stirrer equipped with a stainless steel three propeller blade. A water-soluble conditioning agent was added to the beaker and mixing was continued for at least 15 minutes until all solids were dissolved. Then, the viscosity modifier containing hydroxyethyl acrylate/sodium acryloyldimethyl taurate copolymer, squalane, and polysorbate 60 was added to the beaker, and mixing was continued for at least 15 minutes.

To prepare the base active agent composition, the oil phase beaker was maintained at a temperature between 20° C. and 25° C. The water phase was then slowly transferred to the oil phase beaker under homogenizer agitation, where the transfer time was at least 20 minutes. The homogenizer speed was increased as needed, while maintaining a temperature between 20° C. and 25° C. The resulting water-in-oil emulsion was then covered and mixed for at least 30 minutes. The preservative phase was then added to the beaker while continuing mixing for at least 15 minutes and maintaining a temperature of from 20° C. to 25° C. After ensuring that all powders were off the surface and increasing the mixing speed as needed, zinc oxide particles were added under homogenizer agitation and mixed for at least 5 minutes, increasing the speed as needed and maintaining a temperature of from 20° C. to 25° C. Then the viscosity modifier aluminum starch octenylsuccinate was added under homogenizer agitation and mixed for at least 5 minutes, increasing the speed as needed and maintaining a temperature of from 20° C. to 25° C. Thereafter, fragrance was added to the beaker under homogenizer agitation, and the emulsion was mixed for at least 15 minutes. The resulting base active agent composition had an HLB value of 7.42.

After the base active agent composition was formed, it was filled into an aerosol spray container, after which the container's valve was sealed or crimped to the top of the container. Then, HFO-1234ze propellant was pressure filled via the valve into the container at a pressure of about 200 pounds. The resulting sprayable composition included a substantially homogeneous blend of the propellant and active agent particles, and contained 22 wt. % of the propellant and 78 wt. % of the base active agent composition. The sprayable composition had a specific gravity of about 1.045. The weight percentages of the components used in the sprayable composition are summarized below in Table 1. Once sprayed on a surface (e.g., skin) as a substantially uniform coating, the composition contained 10.4 wt. % of zinc oxide particles due to evaporation of the propellant.

TABLE 1

Sprayable Composition Components
Sprayable Composition

| Component | Wt. % |
|---|---|
| HFO-1234ze | 22.00 |
| Zinc Oxide Particles | 8.11 |
| Polyglyceryl-4 Isostearate; Cetyl PEG/PPG-10/1 Dimethicone; Hexyl Laurate | 0.98 |
| Cetyl PEG/PPG-10/1 Dimethicone | 0.98 |
| Sorbitan Oleate | 0.43 |
| Polysorbate 80 | 0.35 |
| Octyldodecanol/Octyldodecyl Xyloside/PEG-30 Dipolyhydroxystearate | 3.12 |
| Aluminum Starch Octenylsuccinate | 2.34 |
| Hydroxyethyl Acrylate/Sodium Acryloyldimethyl Taurate Copolymer, Squalane, Polysorbate 60 | 0.78 |
| Silicone Oil | 15.60 |
| Water | 29.76 |
| Conditioning Agents | 1.95 |
| Fragrance | 0.16 |
| Freezing Point Depressant | 3.12 |
| Preservatives | 0.20 |
| Emollients | 10.14 |
| Total | 100.00 |

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A spray delivery system comprising a sprayable composition having a viscosity ranging from 1,000 centipoise to 10,000 centipoise, wherein the composition comprises a hydrofluoro-based propellant, a carrier fluid, a non-crosslinked dimethicone polyol, a sorbitan fatty acid ester, and an octyldodecanol, wherein the non-crosslinked dimethicone polyol, the sorbitan fatty acid ester, and the octyldodecanol are nonionic lipophilic emulsifiers each having a hydrophilic to lipophilic balance (HLB) value between 2 and 8: a nonionic hydrophilic emulsifier having a hydrophilic to lipophilic balance (HLB) value between 12 and 19, wherein a weight ratio of the nonionic lipophilic emulsifiers to the nonionic hydrophilic emulsifier ranges from 10 to 20, and active agent particles; and a container, wherein the container comprises a dip tube; a valve assembly comprising a valve body, a stem comprising a stem orifice, and a vapor tap; and an actuator, wherein the dip tube is coupled to the actuator by the valve assembly, wherein the actuator is depressed to dispense the composition stored in the container.

2. The spray delivery system of claim 1, wherein the actuator comprises an exit orifice from which the composition is sprayed.

3. The spray delivery system of claim 2, wherein the exit orifice has a diameter of from 0.3 millimeters to 0.6 millimeters.

4. The spray delivery system of claim 1, wherein the stem orifice has a diameter of from 0.5 millimeters to 0.75 millimeters.

5. The spray delivery system of claim 1, wherein the vapor tap has a diameter of from 0.1 millimeters to 0.5 millimeters.

6. The spray delivery system of claim 1, wherein the composition is introduced to the valve body from the dip tube by the stem orifice, wherein the active agent particles and the propellant are homogeneously dispersed throughout the valve body.

7. The spray delivery system of claim 1, wherein the nonionic hydrophilic emulsifier comprise a sorbitan fatty acid ester modified with a polyoxyethylene.

8. The spray delivery system of claim 1, wherein the composition has a hydrophilic to lipophilic balance (HLB) value of from 2 to 12.

9. The spray delivery system of claim 1, wherein the propellant is present in an amount ranging from 5 wt. % to 95 wt. % and the active agent particles are present in an amount ranging from 0.5 wt. % to 30 wt. % based on the total weight of the composition.

10. The spray delivery system of claim 1, wherein the carrier fluid is a water-in-oil emulsion or an oil-in-water emulsion.

11. The spray delivery system of claim 1, wherein the carrier fluid comprises from 1 wt. % to 35 wt. % of an oil phase and from 1 wt. % to 50 wt. % of a water phase based on the total weight of the composition.

12. The sprayable delivery system of claim 11, wherein the oil phase comprises a silicone oil.

13. The spray delivery system of claim 11, wherein the water phase comprises water.

14. The spray delivery system of claim 1, wherein water is present in an amount of less than 50 wt. % based on the total weight of the composition.

15. The spray delivery system of claim 1, wherein the composition further comprises a viscosity modifier.

16. The spray delivery system of claim 15, wherein the viscosity modifier comprises a carboxylic acid polymer, a starch, or a combination thereof.

17. The spray delivery system of claim 1, wherein less than 3 wt. % of the active agent particles in the composition settle when the composition is stored in a container at 21° C. for 3 days.

18. The spray delivery system of claim 1, wherein the propellant has a first specific gravity and the sprayable composition has a second specific gravity, wherein the ratio of the first specific gravity to the second specific gravity is from 0.7 to 1.6.

19. The spray delivery system of claim 1, wherein the propellant has a vapor pressure of less than 60 psi at 21° C.

20. The spray delivery system of claim 1, wherein the propellant comprises a hydrofluoro-olefin or a hydrofluoro-alkane.

21. The spray delivery system of claim 1, wherein the active agent particles comprise a moisture barrier, antifungal, antibacterial, analgesic, antiseptics, anesthetic, anti-inflammatory, antipruritic, or a combination thereof.

22. The spray delivery system of claim 1, wherein the composition further comprises one or more emollients, conditioning agents, freezing point depressants, preservatives, or a combination thereof.

* * * * *